United States Patent
van Pol et al.

(10) Patent No.: US 11,047,759 B2
(45) Date of Patent: Jun. 29, 2021

(54) SENSOR DEVICE FOR MEASURING FLUID AND FLUID CONDUIT PROPERTIES, AND METHOD FOR ACTIVATING THE SENSOR DEVICE

(71) Applicant: INGU Solutions Inc., Calgary (BA)

(72) Inventors: Johannes Hubertus Gerardus van Pol, Calgary (CA); Anouk van Pol, Calgary (CA); Huibert Aren Bogerman, Ees (NL)

(73) Assignee: INGU Solutions Inc., Calgary (CA)

( * ) Notice: Subject to any disclaimer, the term of this patent is extended or adjusted under 35 U.S.C. 154(b) by 58 days.

(21) Appl. No.: 16/687,742

(22) Filed: Nov. 19, 2019

(65) Prior Publication Data

US 2020/0209093 A1 Jul. 2, 2020

Related U.S. Application Data

(60) Provisional application No. 62/787,604, filed on Jan. 2, 2019.

(51) Int. Cl.
| | |
|---|---|
| *G01L 19/14* | (2006.01) |
| *G01L 19/00* | (2006.01) |
| *G01N 33/18* | (2006.01) |
| *G01L 5/00* | (2006.01) |
| *G01M 3/00* | (2006.01) |

(Continued)

(52) U.S. Cl.
CPC ............ *G01L 19/143* (2013.01); *G01D 5/145* (2013.01); *G01L 19/0092* (2013.01); *G01L 5/008* (2013.01); *G01M 3/005* (2013.01); *G01M 3/246* (2013.01); *G01N 33/1886* (2013.01)

(58) Field of Classification Search
CPC . G01L 19/143; G01L 19/0092; G01L 19/149; G01L 5/008; G01D 5/145; F17D 5/06; F16L 55/40; G01N 33/1886; G01M 3/005; G01M 3/246
See application file for complete search history.

(56) References Cited

U.S. PATENT DOCUMENTS

| | | | | |
|---|---|---|---|---|
| 6,057,773 A | * | 5/2000 | Shukla ................ | B01F 13/0818 200/61.45 R |
| 6,931,952 B2 | * | 8/2005 | Rantala .................. | G01L 5/008 73/431 |

(Continued)

*Primary Examiner* — Jonathan M Dunlap
(74) *Attorney, Agent, or Firm* — Own Innovation; James W. Hinton

(57) ABSTRACT

There is provided a sensor device for measuring fluid and fluid conduit properties, and a method for activating the sensor device. The sensor device comprises an outer capsule for providing fluid-tight containment to an interior compartment of the sensor device in a closed position. The outer capsule comprises a first capsule portion and a second capsule portion. An aperture is located in the second capsule portion and fluidly connects the inner compartment to an exterior of the outer capsule. A mounting bracket is disposed within the inner compartment, the mounting bracket connects the first capsule portion to the second capsule portion and provides structural integrity and pressure resistivity for the outer capsule. At least one pressure sensor is constrained between the mounting bracket and an inner surface of the second capsule portion and is aligned with the aperture of the second capsule portion.

19 Claims, 12 Drawing Sheets

(51) Int. Cl.
*G01M 3/24* (2006.01)
*G01D 5/14* (2006.01)

(56) References Cited

U.S. PATENT DOCUMENTS

| | | | | |
|---|---|---|---|---|
| 6,958,693 | B2 * | 10/2005 | Rothgeb | D06F 34/22 340/539.22 |
| 7,221,323 | B2 * | 5/2007 | Schantz | H01Q 1/36 343/700 MS |
| 8,098,063 | B2 * | 1/2012 | Paulson | F17D 5/00 324/220 |
| 8,939,020 | B2 * | 1/2015 | Townsend | B60C 23/0491 73/146 |
| 9,429,559 | B2 * | 8/2016 | Radjy | G01N 33/383 |
| 9,828,851 | B1 * | 11/2017 | Bonavides | E21B 47/11 |
| 10,324,078 | B2 * | 6/2019 | Ghods | G01N 17/04 |
| 10,591,457 | B2 * | 3/2020 | Radjy | G01N 33/383 |
| 2003/0227394 | A1 * | 12/2003 | Rothgeb | B08B 3/00 340/870.01 |
| 2004/0025607 | A1 * | 2/2004 | Rantala | G01L 19/083 73/866.5 |
| 2005/0010341 | A1 * | 1/2005 | MacNamara | G07C 5/008 701/31.4 |
| 2006/0238422 | A1 * | 10/2006 | Schantz | H01Q 9/00 343/700 MS |
| 2008/0204008 | A1 * | 8/2008 | Paulson | F16L 55/38 324/220 |
| 2014/0150542 | A1 * | 6/2014 | Townsend | B60C 23/0491 73/146 |
| 2015/0212061 | A1 * | 7/2015 | Radjy | G01N 33/383 73/53.01 |
| 2016/0018383 | A1 * | 1/2016 | Radjy | G01N 33/383 73/53.01 |
| 2016/0290964 | A1 * | 10/2016 | Raghavan | H01F 41/071 |
| 2017/0284996 | A1 * | 10/2017 | Ghods | B28C 7/02 |
| 2017/0350241 | A1 * | 12/2017 | Shi | E21B 47/01 |
| 2018/0052146 | A1 * | 2/2018 | Radjy | G01N 33/383 |
| 2020/0093993 | A1 * | 3/2020 | O'Rourke | A61M 5/3202 |

* cited by examiner

SENSOR DEVICE FOR MEASURING FLUID AND FLUID CONDUIT PROPERTIES, AND METHOD FOR ACTIVATING THE SENSOR DEVICE

FIELD

The embodiments disclosed herein relate to a sensor device for measuring fluid and fluid conduit properties, and a method for activating the sensor device.

INTRODUCTION

Sensor devices can be deployed inside of fluid conduits (i.e. pipelines) to collect and analyze fluid and fluid conduit data. A particular challenge faced when deploying sensor devices inside of fluid conduits is that the sensor devices are exposed to high fluid pressures applied by fluid in the fluid conduit. Accordingly, it may be desirable to have a sensor device which is designed for high fluid pressure resistivity.

SUMMARY

There is a sensor device for measuring fluid and fluid conduit properties. The sensor device includes an outer capsule for providing fluid-tight containment to an interior compartment in a closed position, wherein the outer capsule comprises a first capsule portion and a second capsule portion, an aperture located in the second capsule portion and fluidly connecting the inner compartment to an exterior of the outer capsule, a mounting bracket disposed within the inner compartment, the mounting bracket connecting the first capsule portion to the second capsule portion and providing structural integrity and pressure resistivity for the outer capsule, at least one pressure sensor constrained between the mounting bracket and an inner surface of the second capsule portion and aligned with the aperture of the second capsule portion, wherein the pressure sensor senses pressure applied by the fluid to the sensor device, a power source mounted to the mounting bracket and configured to supply power to the sensor device, and a hall effect sensor for activating at least one sensor.

The sensor device may further include a load switch coupled to the power source and the hall effect sensor. The load switch may be configured to activate the power source when the hall effect sensor is activated.

The outer capsule may be configured to withstand pressures of up to 100 bar.

The outer capsule may be formed of fiber-reinforced polymer plastic.

The outer capsule may be formed of fiber-reinforced nylon plastic.

The outer capsule may be formed of material capable of withstanding temperatures of up to 80° C.

The pressure sensor may further include a temperature sensor.

The power source may include non-rechargeable batteries.

The pressure sensor and the hall effect sensor may be coupled to a sensor platform.

The power source may be connected to the sensor platform using one or more conductive strips, the conductive strips pass through the channels and slit passages in the mounting bracket and are soldered to the sensor platform.

The sensor device may include at least one indicator light mounted within the inner compartment, the at least one indicator light indicating the power status of the sensor device.

At least one of the first capsule portion and the second capsule portion may be formed of substantially transparent material.

The sensor device may further include a memory for storing data collected by at least one sensor located in the inner compartment.

The sensor device may further include an add-on system for providing position and tracking sensing of the sensor device.

The material of the first capsule portion and the second capsule portion may be selected for the buoyancy of the sensor device based on the specific gravity of the fluid.

Provided is a method for activating a sensor device for measuring fluid and fluid conduit properties. The method includes placing the sensor device in proximity of a magnetic field, activating a hall effect sensor located within an inner compartment of the sensor device, triggering a load switch coupled to both the hall effect sensor and a power source located in the inner compartment, wherein the load switch switches on the power source, activating a light indicator to indicate that the sensor device is powered on.

The magnetic field may be generated by a permanent magnet.

The sensor device may be placed in proximity of the magnetic field for at least three seconds.

The method may further include inserting the sensor device in a fluid conduit and measuring fluid and fluid conduit data using at least one sensor located in the inner compartment.

The method may further include removing the sensor device from the fluid conduit and retrieving fluid and fluid conduit data from a memory located in the inner compartment.

DRAWINGS

The drawings included herewith are for illustrating various examples of articles, methods, and apparatuses of the present specification. In the drawings.

Figure 1:
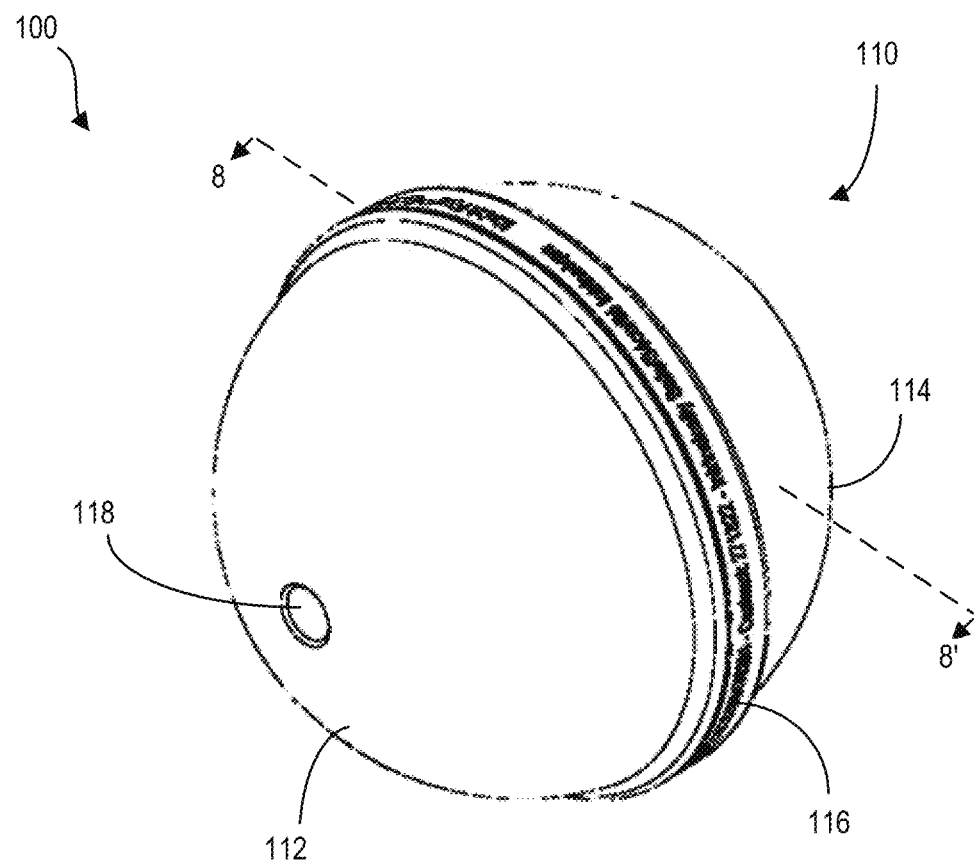
FIG. 1 is a perspective view of an example sensor device, in accordance with an embodiment.
Figure 9A:
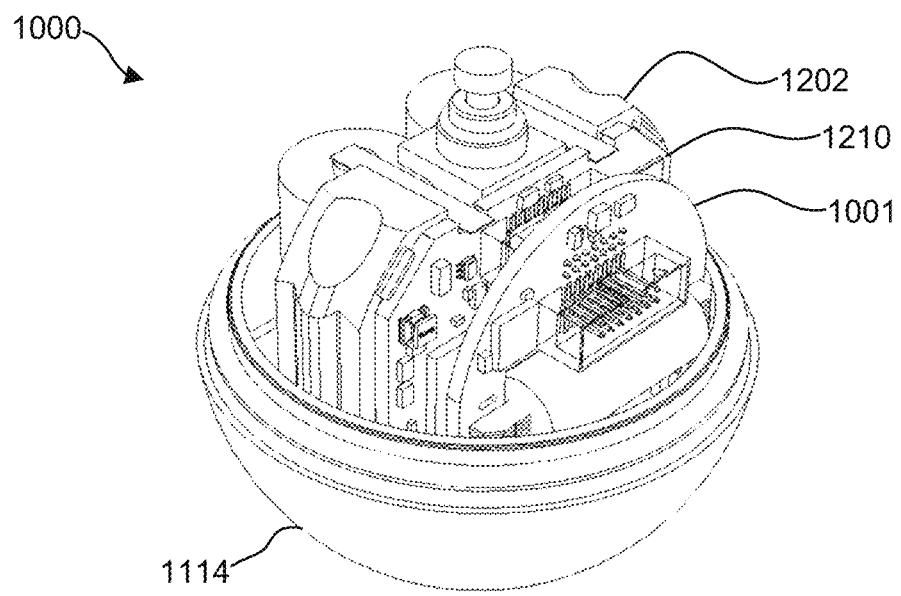
FIG. 9A is a perspective view of a sensor device having an add-on system, with top portion removed, in accordance with an embodiment.
Figure 11:
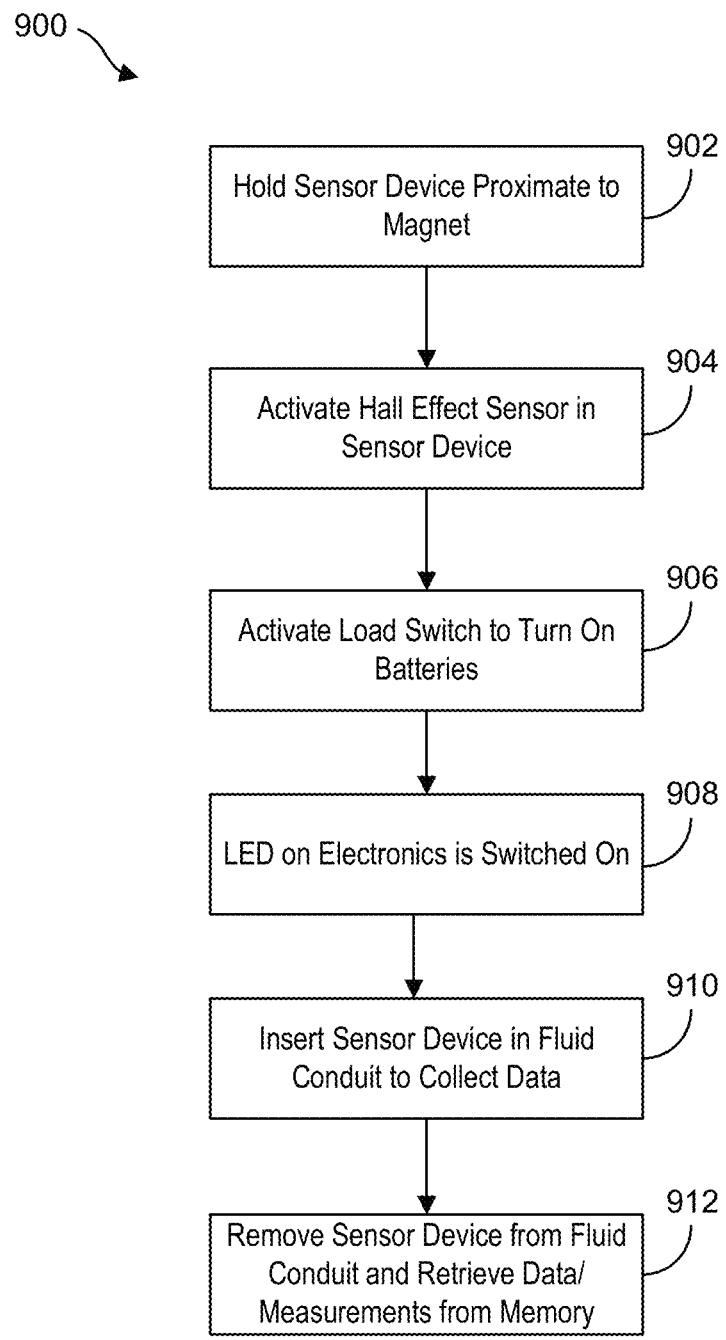

FIGS. 10A, 10B, 10C, and 10D, are perspective and elevation views of the add-on system of the sensor device of FIG. 9A; and FIG. 11 is a flow diagram for an example method for activating the sensor device of FIG. 1.

DESCRIPTION OF VARIOUS EMBODIMENTS

Numerous embodiments are described in this application, and are presented for illustrative purposes only. The described embodiments are not intended to be limiting in any sense. The invention is widely applicable to numerous embodiments, as is readily apparent from the disclosure herein. Those skilled in the art will recognize that the present invention may be practiced with modification and alteration without departing from the teachings disclosed herein. Although particular features of the present invention may be described with reference to one or more particular embodiments or figures, it should be understood that such features are not limited to usage in the one or more particular embodiments or figures with reference to which they are described.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

As used herein and in the claims, two or more parts are said to be "coupled", "connected", "attached", "joined", "affixed", or "fastened" where the parts are joined or operate together either directly or indirectly (i.e., through one or more intermediate parts), so long as a link occurs. As used herein and in the claims, two or more parts are said to be "directly coupled", "directly connected", "directly attached", "directly joined", "directly affixed", or "directly fastened" where the parts are connected in physical contact with each other. As used herein, two or more parts are said to be "rigidly coupled", "rigidly connected", "rigidly attached", "rigidly joined", "rigidly affixed", or "rigidly fastened" where the parts are coupled so as to move as one while maintaining a constant orientation relative to each other. None of the terms "coupled", "connected", "attached", "joined", "affixed", and "fastened" distinguish the manner in which two or more parts are joined together.

Further, although method steps may be described (in the disclosure and/or in the claims) in a sequential order, such methods may be configured to work in alternate orders. In other words, any sequence or order of steps that may be described does not necessarily indicate a requirement that the steps be performed in that order. The steps of methods described herein may be performed in any order that is practical. Further, some steps may be performed simultaneously.

As used herein and in the claims, a group of elements are said to 'collectively' perform an act where that act is performed by any one of the elements in the group, or performed cooperatively by two or more (or all) elements in the group.

As used herein and in the claims, a first element is said to be "received" in a second element where at least a portion of the first element is received in the second element unless specifically stated otherwise.

Some elements herein may be identified by a part number, which is composed of a base number followed by an alphabetical or subscript-numerical suffix (e.g. 112$a$, or 112$_1$). Multiple elements herein may be identified by part numbers that share a base number in common and that differ by their suffixes (e.g. 112$_1$, 112$_2$, and 112$_3$). All elements with a common base number may be referred to collectively or generically using the base number without a suffix (e.g. 112).

Sensor devices can be deployed inside of fluid conduits (i.e. pipelines) to collect and analyze fluid and fluid conduit data. A particular challenged faced when deploying sensor devices inside of fluid conduits is that the sensor devices are exposed to high fluid pressures applied by fluid in the fluid conduit. The word fluid, as used herein, includes fluid in liquid, gas and/or mixture of liquid and gas phases.

Referring now to FIG. 1, there is shown a sensor device 100 for sensing fluid and fluid conduit properties in accordance with an embodiment.

As shown therein, the sensor device 100 may include an outer capsule 110 for providing fluid-tight containment to an interior compartment. The outer capsule 110 may also provide pressure resistivity to the interior compartment against fluid pressure exerted by fluid against the sensor device 100 when the sensor device 100 is deployed inside of the fluid conduit. In various embodiments, the outer capsule 110 is capable of providing pressure resistivity to the interior compartment for pressures of up to 100 bar.

The outer capsule 110 includes a first capsule portion 112 and a second capsule portion 114 that meet at a capsule seam 116 in a closed position. The first and second capsule portions 112, 114 are separable to an open position to provide access to an interior compartment. An aperture 118 is provided in the second capsule portion 114 to expose a pressure and temperature sensor, located inside the inner compartment of the sensor device, to fluid in the fluid conduit.

In various embodiments, the outer capsule 110 is sized to accommodate electrical and hardware components of the sensor device 100, including a power source for the sensor device. In particular, in at least some cases, the outer capsule 110 may have a diameter of at least 3 inches in order to accommodate a large power source which is operable to activate the sensor device 100 for extended durations of time. The outer capsule 110 may have a diameter between 1 and 3 inches. In particular, the outer capsule 110 may have a diameter of 2.2 inches.

The outer capsule 110 is formed from any suitable material which provides fluid-tight containment and pressure resistivity to the interior compartment. For example, the outer capsule 110 may be formed of fiber-reinforced polymer plastic, such as fiber-reinforced nylon plastic. Fiber reinforced plastic may provide the outer capsule 110 with greater structural integrity and high pressure tolerance. In at least some embodiments, the fiber re-enforced polymer plastic can also provide the sensor device with high temperature tolerance. For example, the fiber reinforced plastic may be capable of withstanding temperatures of up to 80*C. The capsule material may also be chemically highly inert to allow the sensor device 110 to withstand chemical features of the medium that the sensor device 100 is deployed in.

In some cases, one or both of the first capsule portion 112 and the second capsule portion 114 may be formed of transparent material, or substantially transparent material. As used herein, transparent material refers to any material that permits at least 50% of light in the visible spectrum to pass through the material. Transparent material may allow a user, of the sensor device 100, to observe inside of the inner compartment of the sensor device 100 when the sensor device 100 is in the closed position of FIG. 1.

The first capsule portion 112 and the second capsule portion 114 may be formed of a material allowing for a range of buoyancies. In particular, the buoyancy of the sensor device 100, including the first capsule portion 112 and the second capsule portion 112, may be in the range of 0.8 to 1.2.

The first capsule portion 112 and the second capsule portion 114 may each be formed of any one or more of Amodel™ AS-1133 HS (Polyphthalamide), Sabic Ultem™ 1000, and Grilamid® TR 90 (Polyamide 12).

Figure 3A:
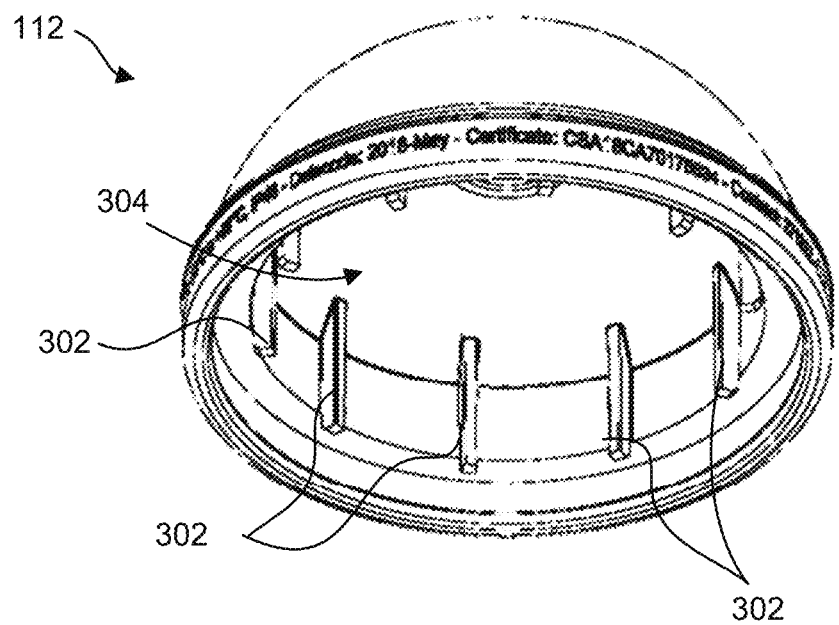
FIG. 3A is a side perspective view of a first capsule portion of the sensor device of FIG. 1.
Figure 3B:
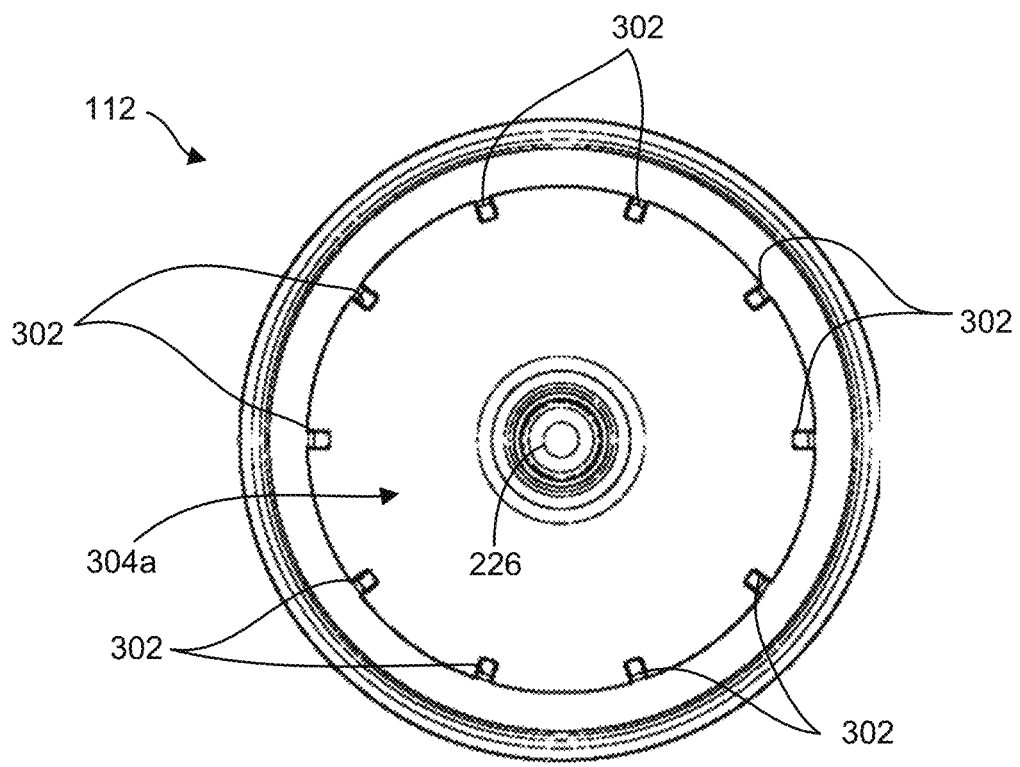
FIG. 3B is a top plan view of the first capsule portion of the sensor device of FIG. 1.

Referring now to FIGS. 3A and 3B, there is shown the first capsule portion 112 of the sensor device 100 in further detail. FIG. 3A shows the first capsule portion 112 in side perspective view. FIG. 3B shows the first capsule portion 112 in top plan view.

As shown therein, the first capsule portion 112 includes a hole 226 for receiving a fastener which may be used to arrange the sensor device 100 in the closed position of FIG. 1. The first capsule portion 112 also includes a plurality of ribs 302 which extend radially inwardly from an inner surface 304a of the first capsule portion 112 and which repeat along the inner circumference thereof. In various embodiments, the ribs 302 are provided to further improve the pressure resistivity feature of the sensor device 100.

Figure 3C:
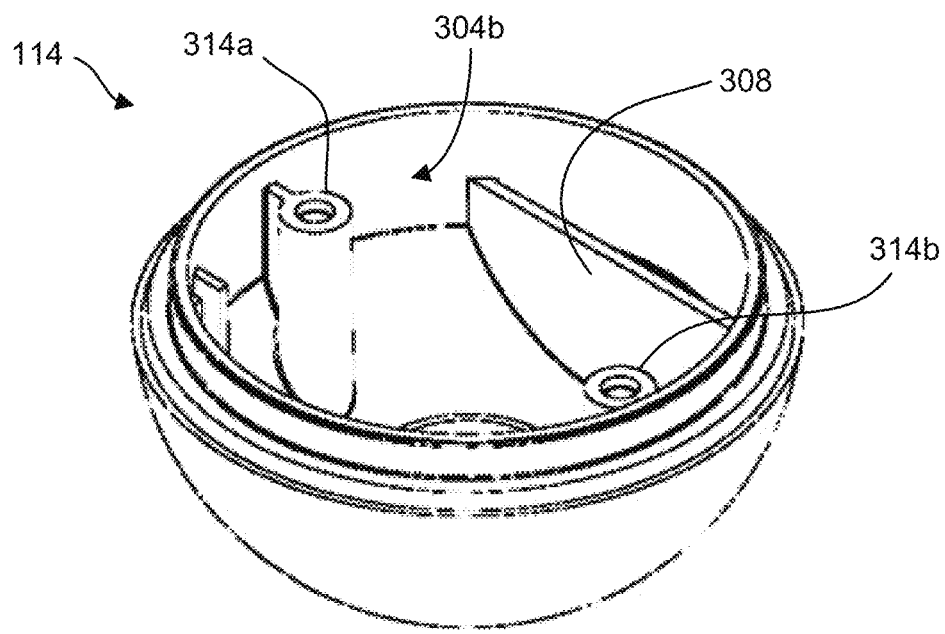
FIG. 3C is a side perspective view of a second capsule portion of the sensor device of FIG. 1.
Figure 3D:
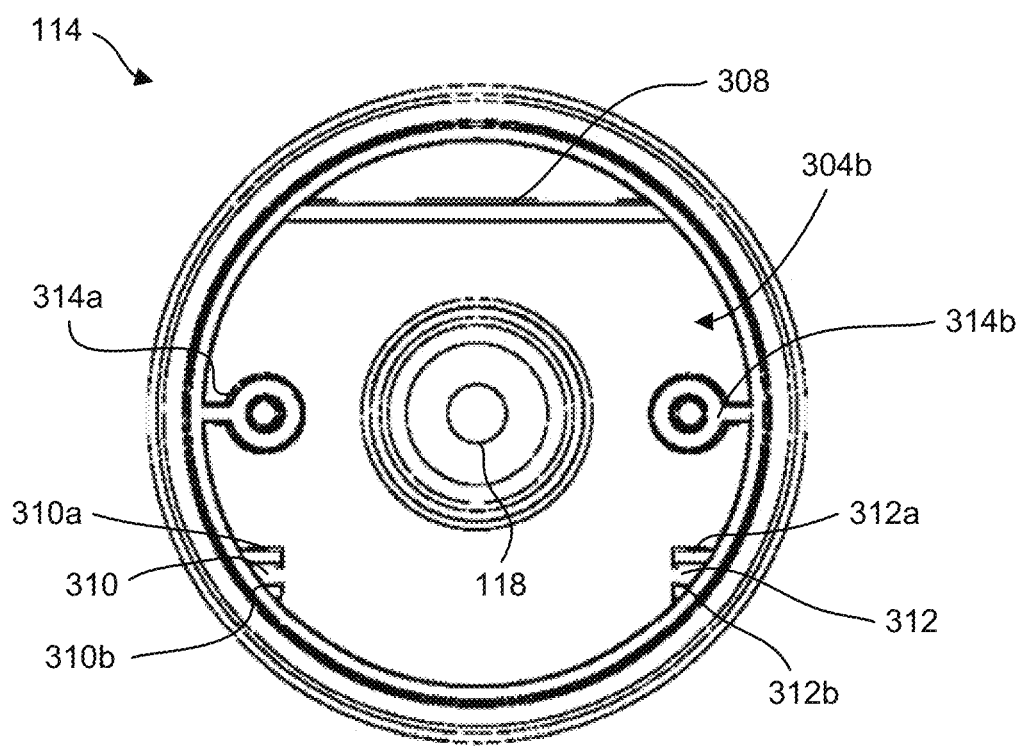
FIG. 3D is a top plan view of the second capsule portion of the sensor device of FIG. 1.

Referring now to FIGS. 3C and 3D, there is shown the second capsule portion 114 in further detail. FIG. 3C shows the second capsule portion 114 in side perspective view. FIG. 3D shows the second capsule portion 114 in top plan view.

As shown, the second capsule portion 114 includes a first column-formed bore 314a and a second column-formed bore 314b, each which extend upwardly from an inner surface 304b of the second capsule portion 114. As explained herein, each of the first and second column-formed bores 314a, 314b are also configured to receive fasteners which are used to arrange the sensor device 100 into the closed position of FIG. 1.

The second capsule portion 114 also includes a vertical support plate 308. In various embodiments, the vertical support plate 308 may act as a back-support for a power source located in the sensor device 100.

The second capsule portion 114 also includes two slits 310, 312 formed from oppositely facing member plates 310a, 310b and 312a, 312b, respectively, which extend upwardly from the inner surface 304b. The slits 310, 312 receive and vertically support a density matching weight located in the inner compartment of the sensor device 100.

The slits 310, 312 may also support an add-on circuit board to extend functionality. The add-on circuit board may be, for example, a tracking system, or a global positioning system (GPS) receiver (for example, FIGS. 9A-10D).

Where the sensor device 100 includes an add-on circuit board (e.g., FIGS. 9A-10D), the compartment behind the vertical support plate 308 may hold a density matching weight 216. The density matching weight 216 is placed behind the vertical support plate 308, to provide that the sensor device 100 is oriented in the fluid in the same way.

The weight 216 may provide that battery side of the sensor device 100 will continue to be oriented at the bottom of the sensor device 100, when the sensor device 100 is free-floating. In contrast, if a weight were positioned on the opposite side of the batteries, the balance of the sensor device 100 may be undesirably tilted.

The aperture 118 is centrally disposed within the second capsule portion 114. As explained previously, the aperture 118 aligns with a pressure and temperature sensor located in the inner compartment of the sensor device 100 and is used to expose the pressure and temperature sensor to fluid in the fluid conduit (i.e. to record pressure applied by the fluid on the sensor device, as well as to monitor fluid temperature).

Figure 2:
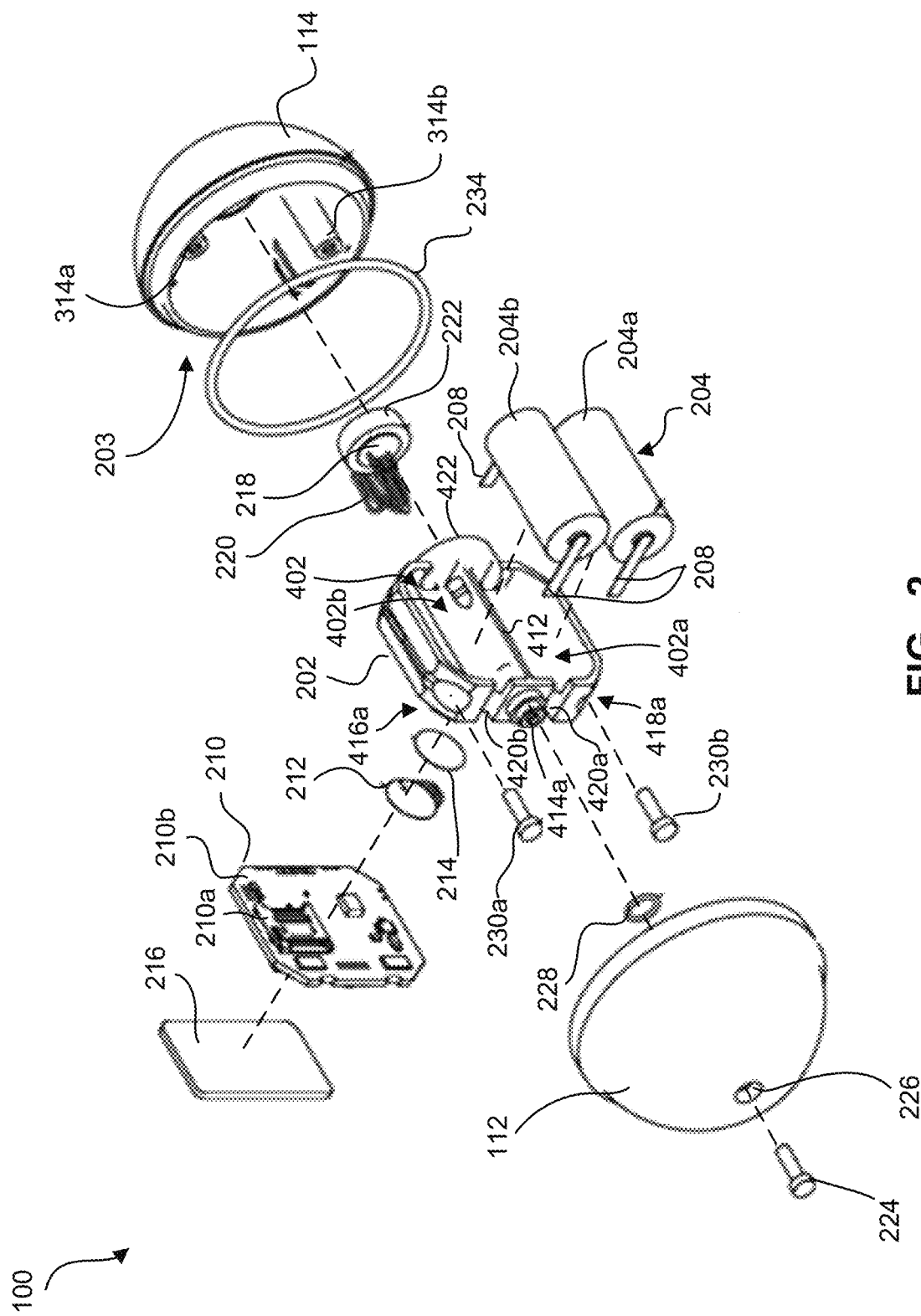
FIG. 2 is an exploded view of the sensor device of FIG. 1.

Referring now to FIG. 2, there is shown an exploded view of the sensor device 100 of FIG. 1 and illustrating the various electrical and mechanical components which may be carried within the inner compartment of the sensor device 100.

As illustrated, the sensor device 100 includes a central mounting bracket 202 which may be physically installed in, and removed from, an interior compartment 203 of the sensor device 100. In various embodiments, the mounting bracket 202 provides a resilient structure which aggregates, in a space-efficient manner, the various hardware located in the sensor device 100. Additionally, the bracket 202 is positioned, and engaged, between the first and second capsule portions 112, 114, to provide an internal support framework for the sensor device 100 which accordingly further improves the pressure resistivity feature of the sensor device 100.

Figure 4A:
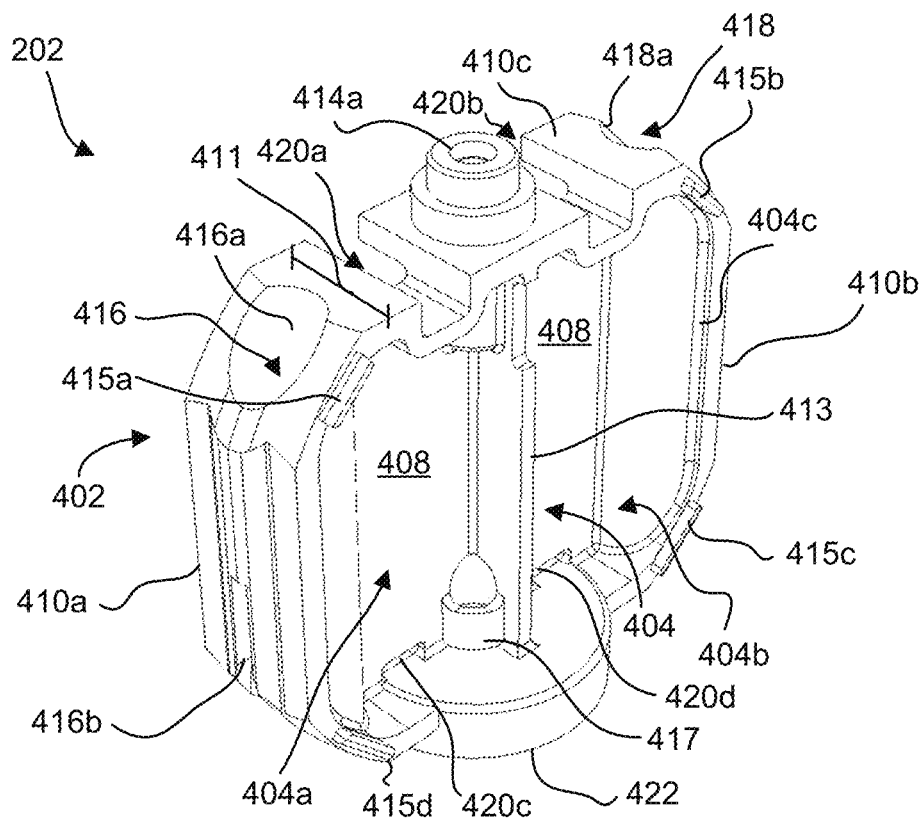
FIG. 4A is a perspective view of a mounting bracket.
Figure 4B:
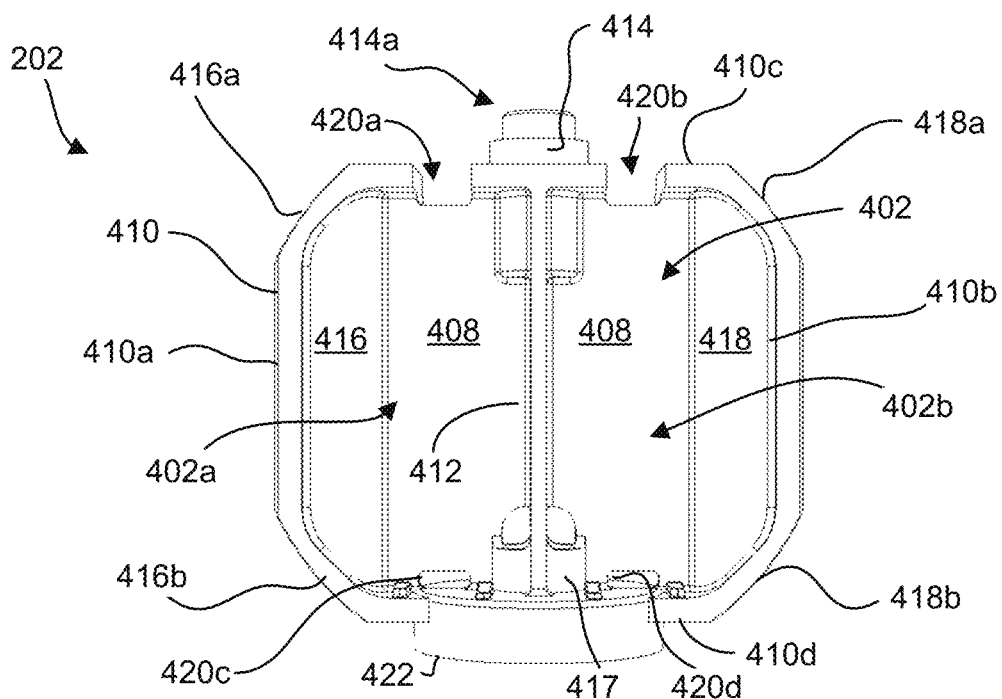
FIG. 4B is a front elevation view of the mounting bracket of FIG. 4A.

Referring now briefly to FIGS. 4A and 4B, there is shown the central mounting bracket 202 in further detail. In particular, FIG. 4A shows the mounting bracket 202 in side perspective view. FIG. 4B shows the mounting bracket 202 in front elevation view.

As illustrated, the bracket 202 includes a separation wall (or surface) 408, and an outer perimeter frame 410 which extends at least partially forwardly and rearwardly from the separation wall 408 to an extent defined by a lateral width 411. The forward and rearward extensions of the frame 410 from the separation wall 408 define (or form) a first bracket recess 402 (or a front facing bracket recess 402, or a front bracket side 402), and a second bracket recess 404 (or a rear facing bracket recess 404, or a rear bracket side 404). The bracket recesses 402, 404 are separated from each other at least by the separation wall 408. The outer perimeter frame 408 is generally defined by a first lateral surface 410a, and a distally opposed second lateral surface 410b, as well as a top surface 410c, and a distally opposed bottom surface 410d. Each of the lateral surfaces 410a, 410b, and the top and bottom surfaces 410c, 410d may have a width defined at least by the lateral width 411.

As described in further detail herein, the first bracket recess 402 may receive (e.g. mount) a power source for the sensor device 100, while the second bracket recess 404 may receive (e.g. mount) mechanical and electronic hardware of the sensor device 100. To this end, the separation wall 408 may be formed of a non-conductive surface which protects and/or prevents the electronic components located in the second bracket side 404 from shorting with the power source located in the first bracket recess 402. The separation wall 408 also enhances the structural integrity and pressure resistivity features of the bracket 202, and by extension, the structural integrity and pressure resistivity feature of the sensor device 100.

In at least some embodiments, the first bracket recess 402 may also include a first partition member 412 extending forwardly from the separation wall 408 and spanning between the top surface 410c and the bottom surface 410d of the frame 410. The first partition member 412 may accordingly partition the first bracket recess 402 into a first sub-recess 402a and a second sub-recess 402b. As explained herein, the first and second sub-recess 402a, 402b may receive separate power sources of the sensor device 100. The first partition member 412 may also be used to further enhance the structural integrity, and pressure resistivity, of the bracket 202 and the sensor device 100. In some cases, a second partition member 413 may extend rearwardly from the separation wall 408 to similarly segment the second bracket recess 404 into two sub-recess portions. The first partition member 412 and the second partition member 413 may also provide support to the centerline of the circuit board.

The top surface 410c of the frame 410 includes an opening 414a in fluid communication with a top surface aperture 414. The top surface aperture 414 may extend partially downwardly into the bracket 202 (i.e. in the direction of the bottom surface 410d) before intersecting the first partition member 412. As explained herein, the top surface aperture 414 is configured to receive a threaded fastener (e.g. a bolt, a rivet, a screw) which secures the bracket 202 to the first capsule portion 112. The outer perimeter frame 410 also included a first side bore 416 and a second side bore 418, each being configured to receive threaded fasteners (e.g. bolts, rivets, screws) for securing the bracket 202 to the second capsule portion 114.

The first side bore 416 extends parallel to (and behind) the first lateral surface 410a, between the top surface 410a and the bottom surface 410d of the frame 410. The first side bore 416 includes a top opening 416a—located at the intersection of the top surface 410c and first lateral surface 410a—and a bottom opening 416b—located at the intersection of the first lateral surface 410a and the bottom surface 410d.

Similarly, the second side bore 418 extends parallel to (and behind) the second lateral surface 410b, and also between the top surface 410a and the bottom surface 410d of the outer perimeter frame 410. The second side bore 418 includes a top opening 418a—located at the intersection of the top surface 410c and second lateral surface 410b—and a bottom opening 418b—located at the intersection of the second lateral surface 410b and the bottom surface 410d.

Still referring to FIGS. 4A and 4B, in various embodiments, the top surface 410c includes a first channel 420a and a second channel 420b, wherein the channels 420a, 420b span the width 411 of the top surface 410c and are located on opposite sides of the top aperture 414. As explained herein, the first and second channels 420a, 420b receive conductive strips which connect a power source, located in the first bracket recess 402, to electrical hardware, located in the second bracket side 404.

The central mounting bracket 202 includes notches 415a, 415b, 415c, and 415d for engaging with a sensor platform 210. The notches 415a, 415b, 415c, and 415d are on the corners of surface 410 to prevent the sensor platform 210 from rotating or moving. The sensor platform 210 is held to the bracket 202 by the conductive strips to the batteries.

The bracket 202 includes a collar 417 the improve pressure resistivity of the bracket 202. The collar 417 passes from the separation wall 408 to the first partition member 412 and from the separation wall 408 to the second partition member 413.

In an embodiment, the power source includes a plurality of power sources. This may advantageously provide increased power as well as facilitate buoyancy.

The bracket 202 also includes a first slit passage 420c and a second slit passage 420d, located above the bottom surface 410d of the frame 410. The slit passages 420c and 420d also provide further conduits for conductive strips which connect to a power source. In at least some embodiments, the first and second channels 420a, 420b receive conductive strips which connect to a cathode of the power source, while slit passages 420c, 420d receive conductive strips which connect to an anode of the power source (or vice-versa).

A circular recess formed by a hollow annular member 422 is located on the bottom surface 410d of the frame 410. In accordance with the teachings provided herein, the annular member 422 is configured to receive and secure a pressure and temperature sensor of the sensor device 100 into engagement with an inner surface of the second capsule portion 114 and into alignment with the aperture 118 of the second capsule portion 114.

Referring now back to FIG. 2, as explained previously, the first bracket recess 402 may receive (e.g. mount) a power source 204 of the sensor device 100. The power source 204 may be any power source that is configured to supply power to electrical hardware located in the sensor device 100. In the illustrated embodiment, the power source 204 includes a pair of batteries (e.g. a first battery 204a, and a second battery 204b) which supply power to the sensor device 100 for an extended duration of time.

In at least some embodiments, the batteries 204a, 204b may be non-rechargeable batteries. The batteries 204a, 204b may be configured to supply continuous power to the sensor device for a duration of at least 8 hours when activated. Where there is one power source 204, the sensor device may receive power for 8 hours. Where there are two batteries 204a, 204b, the sensor device may receive power for 28 hours.

The sensor device may also include load switches which are used for activating the batteries. The batteries 204a, 204b may be characterized by having low leakage current and long shelf life. For example, the batteries 204a, 204b may have a shelf life of over 10 years. The sensor device may have a shelf life of 1 year with a leakage current of less than approximately 5 uA.

Where the bracket 202 includes the first partition member 412, the first battery 204a may be received in the first sub-recess 402a, while the second battery 204b may be received in the second sub-recess 402b.

Conductive strips 208 are coupled to the respective cathode and anode ends of each battery 204. The conductive strips 208 are received within, and extend across, the first and second channels 420a, 420b of the mounting bracket 202, as well as the first and second slit passages 420c, 420d. In at least some embodiments, the conductive strips 208 are guided through the channels 420a, 420b and the slit passages 420c, 420d, and soldered to the sensor platform 1210.

The second bracket side 404, of the mounting bracket 202, may receive electronic components which are powered by the power source 204. For example, the second bracket side 404 may receive a sensor platform 210. The sensor platform 210 may receive power from the power source 204 via the conductive strips 208 which extend across the channels 420a, 420b, and the slit passages 420c, 420d.

In various embodiments, the sensor platform 210 is provided to support the various sensors that may be included in the sensor device 100 and components that support the operation of the various sensors. The sensor platform 210 may be provided on a printed circuit board with soldered components. Sensors which may couple to the sensor platform 210 may include sensors for measuring, for example, linear motion, temperature, magnetic field, etc. In at least some embodiments, the sensor platform 210 also provides a mount for an acoustic sensor 212 which senses acoustic properties of a fluid in a fluid conduit.

The sensors may measure the acoustic properties of leaks. The sensors may measure any one or more of the fluid conduit, the pumps, and the pipeline roughness. The sensors may sense an anomalous signal in the acoustic properties of the fluid.

The acoustic sensor 212 may include, for example, a piezo transducer. The piezo transducer may convert the vibration of the outer capsule 110 of the sensor device 100 to electrical signals as known in the art. Electrical signals are received by the sensor platform 210 for further processing. The acoustic sensor 212 can also be used for, e.g., detecting presence of a leak within the fluid conduit and size of the detected leak. The acoustic sensor 212 may be attached to the bracket 202 through an epoxy resin 214.

The sensor device 100 may be single use. The sensor device 100 may have a limited shelf life (e.g., 1 year), and after the sensor device 100 has been activated, the sensor device 100 run for a period of time (for example, at least 24 hours) after which the sensor device 100 has a controlled shutdown. Once activated, the sensor device 100 may not be turned off. By design, the sensor device 100 may run until the power source has been depleted or where a set software runtime has expired.

In at least some embodiments, the sensor platform 210 may also include a hall effect sensor. The hall effect sensor may be a component of the sensor platform 210. As explained herein, the hall effect sensor may be used to activate the power source 204 of the sensor device 100 when the sensor device 100 is placed in proximity to a magnet. This has the advantage of allowing remote (or external) activation of the sensor device 100 without requiring the sensor device 100 to be dis-assembled, and re-assembled, to turn on the sensor electronics. In particular, the hall effect sensor may be connected to a load switch of the power source 204. When the hall effect sensor is activated, the load switch is turned ON, and the power source is connected to the sensor platform 210. In some cases, an indicator light (i.e., such as an LED light) may be provided on the sensor platform 210. The indicator light might turn ON when the sensor electronics are activated. Accordingly, a user may perceive the indicator light if the outer capsule 110 is made from transparent, or substantially transparent, material.

The sensor platform 210 can also include a memory integrated with the sensor platform 210. The memory stores measurements collected by the various sensors of the sensor device 100. The memory may receive data from the sensors via a processor.

The memory may be a uSD card memory module that is soldered directly into the sensor platform 210. The sensor platform may have a fixed memory and may be connected to a device (i.e. computer) by the use of a USB port 210b provided on the sensor platform to access the fixed memory.

In some embodiments, the memory may be removable and/or swappable. For example, the memory may be an SD or microSD memory card fitted to an appropriate interface, such as a memory card slot 210a. The memory card may be removed from the memory card slot 210a and received by a computer to access stored data (i.e., sensor measurements). The sensor platform 210 may be configured to allow a user to elect, or choose, from one of a variety of ways to access the memory of the sensor device 100.

The sensor device 100 also includes a density matching weight 216 which may be positioned behind (but otherwise disconnected from) the sensor platform 210. The density matching weight 216 is used to achieve neutral buoyancy of the sensor device 100 in different types of fluid. To this end, the density matching weight 216 may be selected a priori to accommodate for a known density property of a known fluid in which the sensor device 100 will be placed. For example, in some embodiments, the density matching weight 216 can be used to help in adjusting the vertical location of the sensor device 100 within the fluid conduit. For example, the sensor device 100 can flow lower in a fluid conduit by increasing the weight of the density weight 216.

The first capsule portion 112 and the second capsule portion 114 may be formed of materials in order to match the density of the fluid.

Alternatively, the sensor device 100 can flow higher in the fluid conduit by decreasing the weight of the density weight 216. Accordingly, information about different heights within a pipeline may be gathered. In addition, when the sensor device 100 is made to flow closer the bottom of the fluid conduit, it may collect more information regarding the fluid and the conduit in that lateral location. For example, when the fluid comprises of a multiple layers of fluids, by adjusting the weight and thereby the vertical location of the sensor device 100 within the fluid conduit, the sensor device 100 can collect information about the boundaries between the layers, shear force between the boundaries, differences between layers' flow speeds, presence of water in an oil pipeline, presence of gaseous particles such as air in the pipeline, etc.

Still referring to FIG. 2, an external-facing pressure and temperature sensor 218 is disposed inside of the internal compartment 203 of the sensor device. In particular, the sensor 218 is received within the hollow annular member 422 of the bracket 202. The annular member 422 securely holds (or presses, or sandwiches) the sensor 218 against the inner surface of the second capsule portion 114 and into alignment with the aperture 118 of the second capsule portion 114. By pressing the sensor 218 against the inner surface of the second capsule portion 114, the sensor is more rigidly (e.g. resiliently) secured within the inner compartment and may withstand large magnitudes of fluid pressure applied against the sensor device 100. An O-ring seal 222 is provided to seal the pressure and temperature sensor 218 and prevent fluid from entering the sensor device 100 through the aperture 118. The pressure and temperature sensor 218 may also include a set of wires 220 which connect to the sensor platform 210. In some embodiments, the pressure sensor 218 may record fluid pressure of up to 100 bar, and measure fluid temperatures of up to 80° C.

In order to assemble the sensor device 100 into the closed position of FIG. 1, the bracket 202 is placed in the bottom shell (second capsule 114) and then threaded fasteners 230 are put in place.

The sensor device 100 includes threaded fasteners 230a and 230b (e.g. bolts, rivets, screws). The threaded fastener 230a is first received into the top opening 416a, of the first side bore 416, of the bracket 202. The fastener 230a is then engaged—from the bottom opening 416b of the first side bore 416—with the first column-formed bore 232a of the second capsule portion 114. Likewise, the threaded fastener 230b is received into the top opening 418a, of the second side bore 418, of the bracket 202. The fastener 230a is then engaged—from the bottom opening 418b of the second side bore 418—with the second column-formed bore 232b of the second capsule portion 114. Each of column-formed bores 232a, 232b is accordingly axially aligned with the bottom opening of the first and second bores 416, 418 of the bracket 202.

After the bracket 202 is secured to the second capsule portion 114, the first capsule portion 112 is secured to the bracket 202. To this end, the sensor device 100 includes a fastener 224 (e.g. a bolt, a rivet, a screw) which is received in the hole 326 of the first capsule portion 112. The fastener 224 extends through the hole 326 and into threaded engagement with the top surface aperture 414 of the bracket 202. A sealing O-ring 228 may be disposed between the opening 414a, of the top surface aperture 414 and the hole 326 to provide for water-tight sealing.

When dis-assembling the sensor device 100, the first shell portion is first de-coupled from the bracket 202 by removing the fastener 224. The second shell portion is subsequently de-coupled from the bracket 202 by removing the fasteners 230a, 230b.

The sensor device 100 may also include an O-ring seal 234 for sealing the capsule seam 116 and providing further water-tight sealing to the sensor device 100.

Figure 5A:
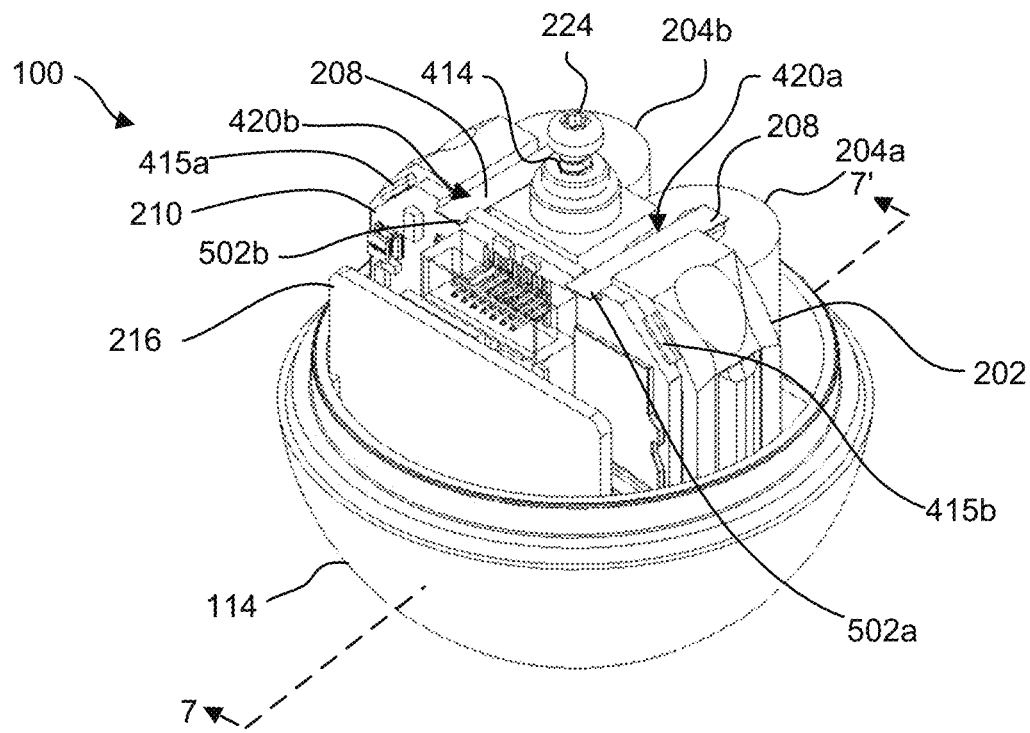
FIGS. 5A and 5B are perspective views of the sensor device of FIG. 1 with the first capsule portion removed to expose the interior compartment of the sensor device.
Figure 5B:
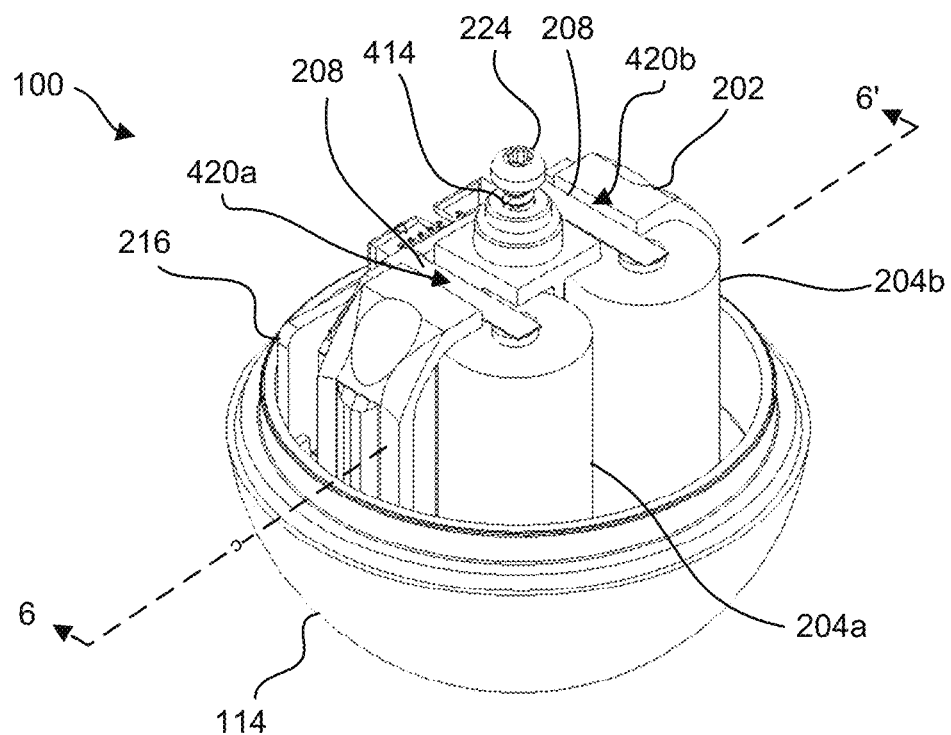

Referring now to FIGS. 5A and 5B, there is shown a perspective view of the sensor device 100 of FIG. 1 with the first capsule portion 112 removed to expose the interior compartment of the sensor device.

As shown therein, the batteries 204a, 204b are positioned on one side of the bracket 202, in the first bracket recess 402, and the sensor platform 210 is positioned on the opposite side of the bracket 202, in the second bracket side 404. The sensor platform 210 receives power from the batteries 204a, 204b via the conductive strips 208 which extend across the channels 420a, 420b and connect with the sensor platform 210 at electrical contact points 502a, 502b, respectively. The density weight 216 is shown as disposed rearwardly from the sensor platform 210.

Figure 6:
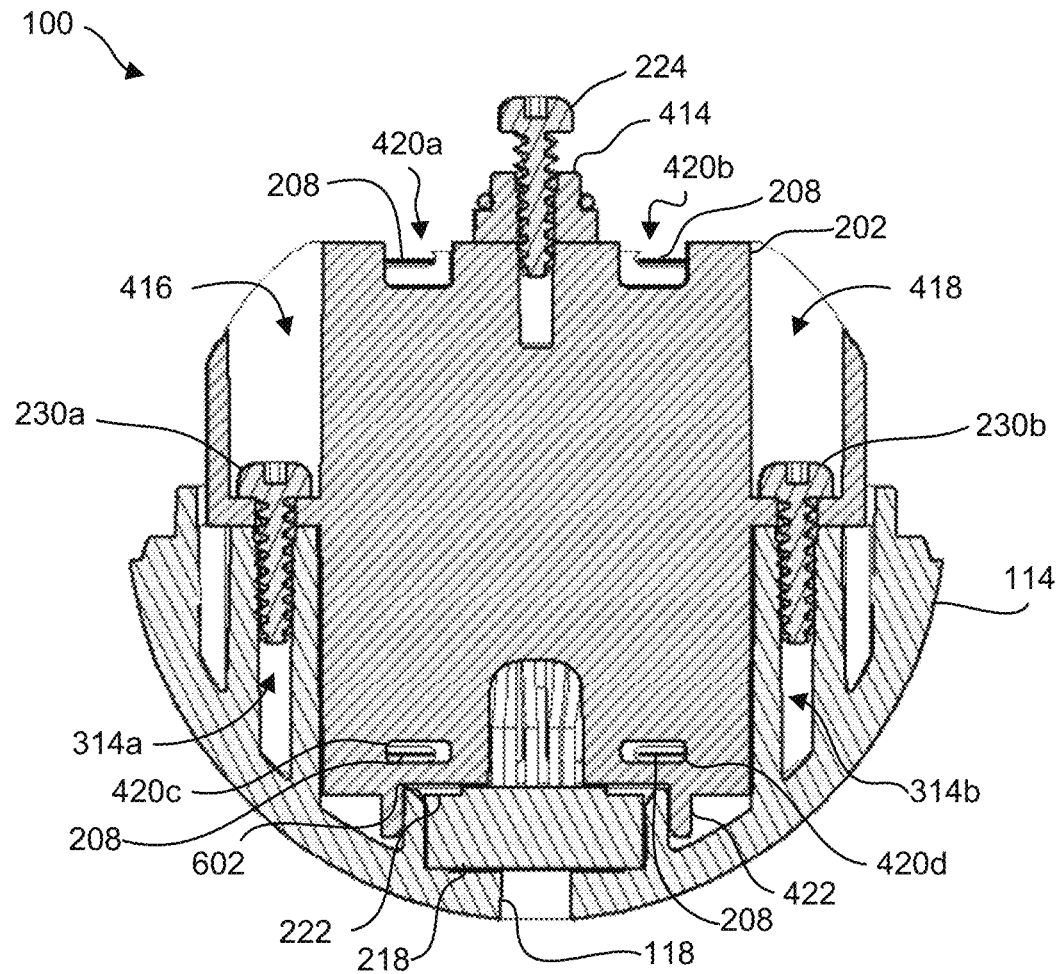
FIG. 6 is a cross-sectional view of the sensor device of FIG. 5B along the cross-section line 6-6' of FIG. 5B.

Referring now to FIG. 6, there is shown a cross-sectional view of the sensor device 100 along the cross-section line 6-6' of FIG. 5B.

As illustrated, the bracket 202 is secured to the second capsule portion 114 by inserting the threaded fasteners 230a, 230b through the first side bore 416 and second side bore 418 of bracket 202, respectively, and into threaded engagement with the respective column-formed bores 314a, 314b of the second capsule portion 114. Also shown therein, the pressure and temperature sensor 218 is pressed between the hollow annular member 422 of the bracket 202, and an inner surface of the second capsule portion 114 and into alignment with the aperture 118 thereof. As mentioned, this configuration allows for the pressure and temperature sensor 218 to be resiliently and mechanically secured within the inner compartment to withstand high pressure forces applied by fluid, in the fluid conduit, against the pressure and temperature sensor 218. The second capsule portion 114 also includes a hollow circular member 602 which also securely receives, and positionally aligns, the pressure and temperature sensor 218 within the inner compartment.

Figure 7:
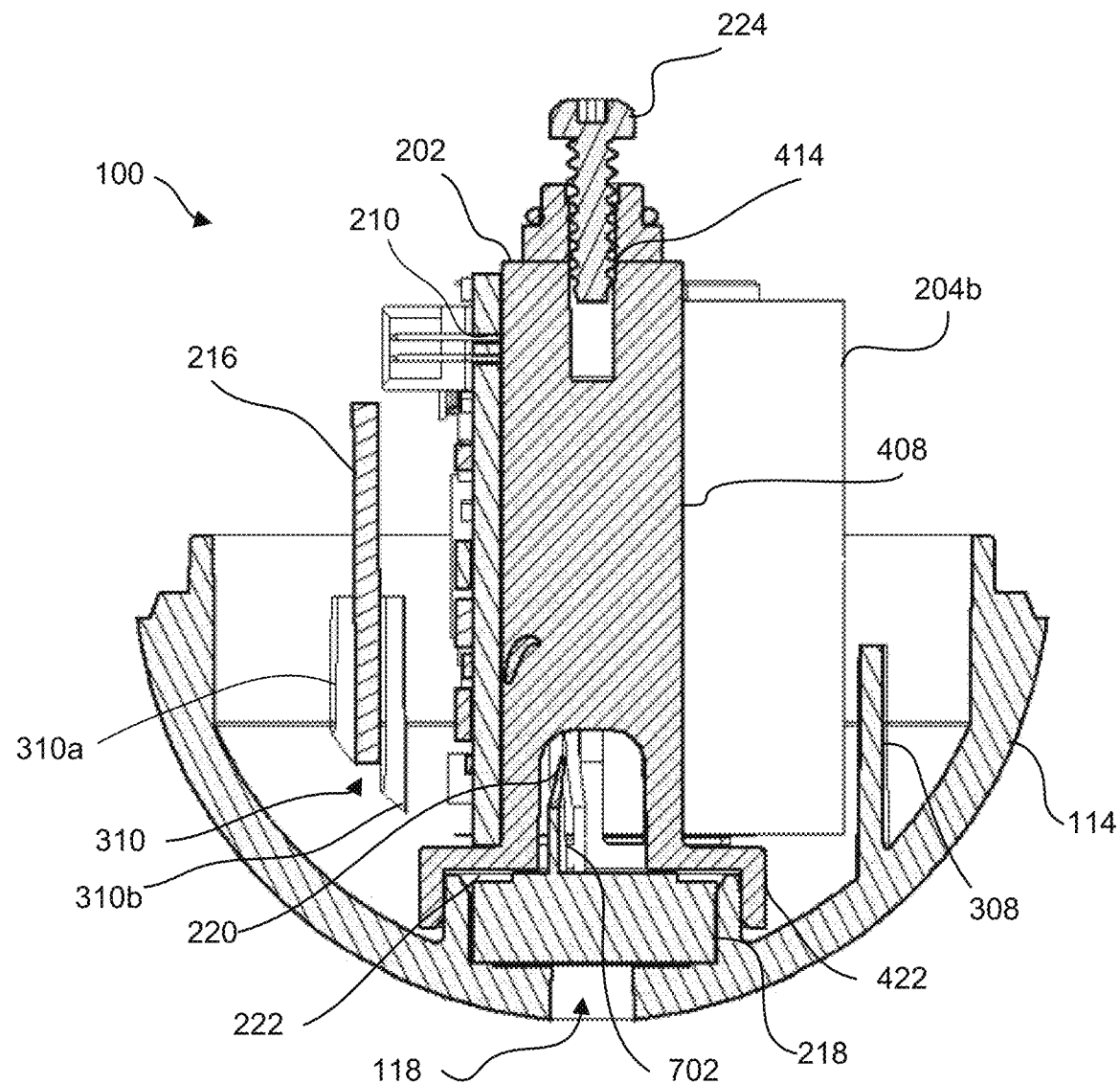
FIG. 7 is a cross-sectional view of the sensor device of FIG. 5A along the cross-section line 7-7' of FIG. 5A.

Referring now to FIG. 7, there is shown a cross-sectional view of the sensor device 100 along the cross-section line 7-7' of FIG. 5A.

As illustrated, the battery 204a is positioned on one side of the separation wall 408 of the bracket 202, while the sensor platform 210 is positioned on the opposite side of the separation wall 408. Further, the density matching weight 216 is held in place by the oppositely facing member plates 310a, 310b forming the slit 310. The wires 220 of the pressure/temperature sensor 218 extend through a recess 702 formed below the separation wall 408 of the bracket 202 to connect with the sensor platform 210.

Figure 8:
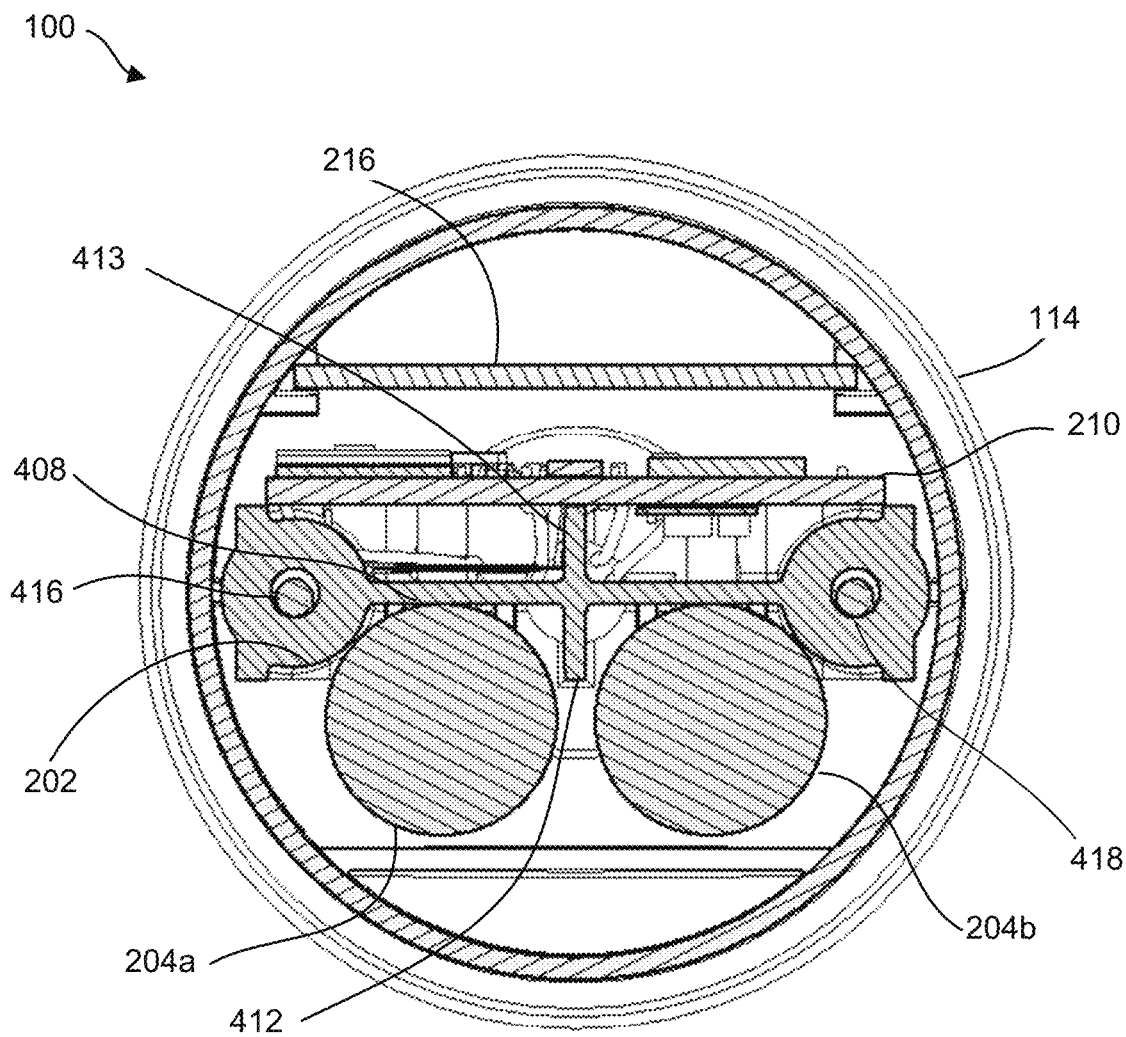
FIG. 8 is a cross-sectional view of the sensor device of FIG. 1 along the cross-section line 8-8' of FIG. 1.

Referring now to FIG. 8, there is shown a cross-sectional view of the sensor device 100 along the cross-section line 8-8' of FIG. 1.

As shown, the batteries 204a, 204b are each located on opposing sides of the first partition member 412, and on the opposite side of the separation wall 408 from the sensor platform 210. As well, the density matching weight 216 is located rearwardly from the sensor platform 210. The bracket 202 may also include the second partition member 413 which extends rearwardly from the separation wall 408 and into the second bracket recess 404.

Figure 9B:
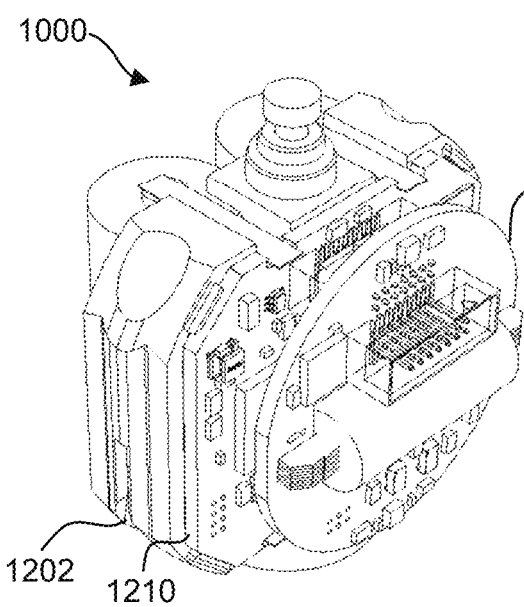
FIGS. 9B and 9C are elevation and perspective views, respectively, of the sensor device of FIG. 9A, with the first and second capsule portion removed.
Figure 9C:
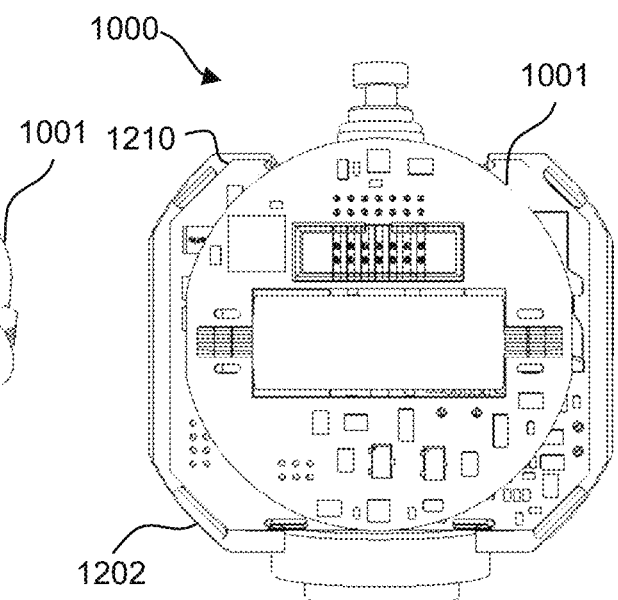
Figure 10A:
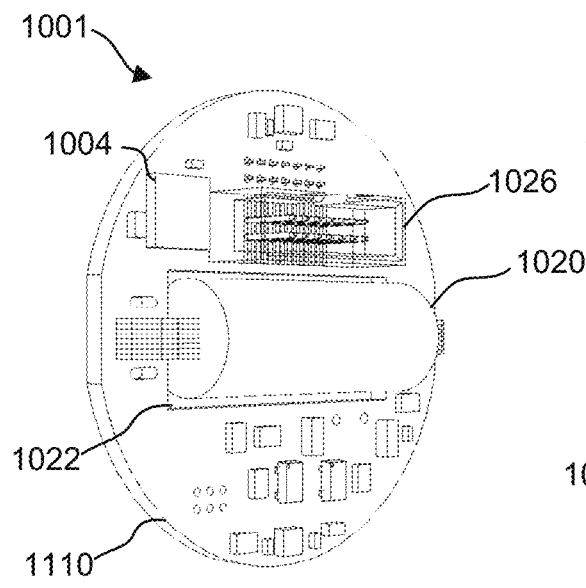
Figure 10B:
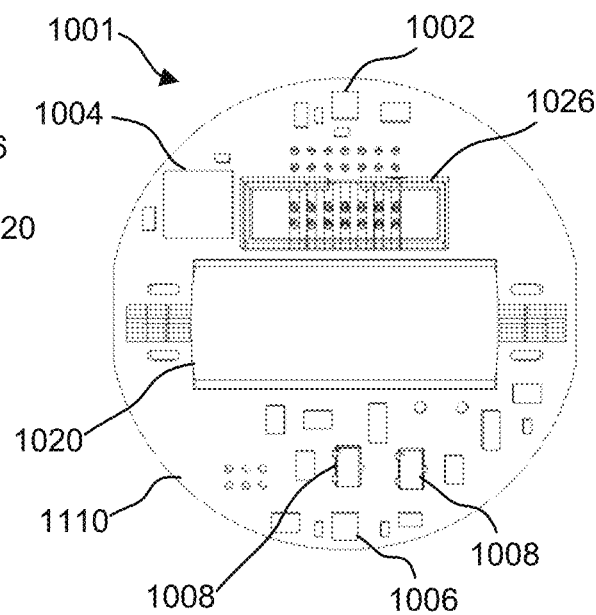
Figure 10C:
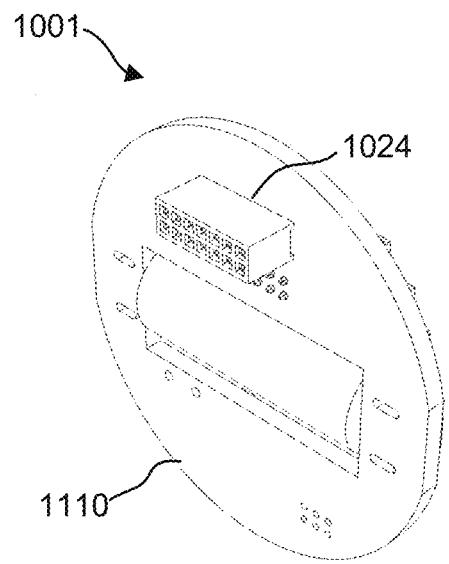
Figure 10D:
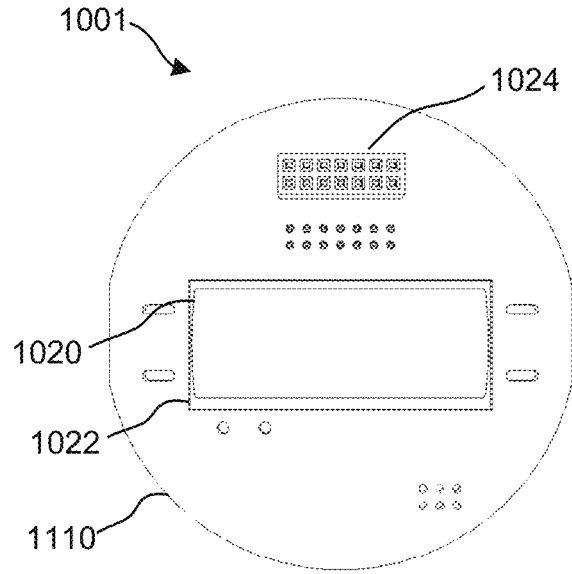

Referring now to FIGS. 9A to 9C, illustrated therein is a sensor device 1000, in accordance with a further embodiment. The sensor device 1000 includes an add-on system 1001 for supplying additional capability to the sensor device 1000. The add-on system 1001 is capable of transmitting an electro-magnetic signal that can be detected by an external receiver to verify if the sensor device 1000 is at a predetermined location. The add-on system 1001 may include any one or more of a tracker system, a GPS system, magnetic sensors, and other additional sensors.

The add-on system 1001 is in addition to a main sensor platform 1210 (for example, sensor platform 210). The add-on system 1001 may be positioned in place of or in addition to a weight (e.g., weight 216 of FIG. 5A). The add-on system 1001 may be removably positioned in a bottom portion 1114 of the sensor device 1000. The add-on system 1001 is attached to outer shell 1114 (for example in slits 310, 312) and not to a central mounting bracket 1202.

Referring now to FIGS. 10A-10D, illustrated therein is the add-on system 1001. The add-on system 1001 includes a circuit board 1110 for supporting components of the add-on system 1001. The circuit board 1110 is circular shaped to fit into the spherical sensor device 1000 and be held by the sensor device 1000.

The add-on system 1001 may include at least one GPS sensor (for example, a positions sensor, not shown) attached to the circuit board 1110. The GPS sensor senses position information of the sensor device 1000.

The add-on system 1001 may include a first magnetometer 1002 and a second magnetometer 1008. The magnetometers 1002, 1006 sense magnetic information. The magnetic information is collected by processor 1004 and sent to sensor platform 1210 for storage. Velocity of the sensor device maybe determined by combining the sensed magnetic information and data from the IMU on the sensor platform 1210. Velocity may be determined from the sensor device. The add-on system 1001 may use power provided by the sensor platform 1210.

The add-on system 1001 may include a transmitter coil 1020 attached to the circuit board 1110. The transmitter coil 1020 generates an electro-magnetic signal that may be received by an external receiver. The transmitter coil 1020 is driven by processor 1004 through mosfets 1008. The circuit board 1110 may include an aperture 1022 central to the circuit board 1110 for receiving the transmitter coil 1020.

The add-on system 1001 may also include a sensor device connection port 1024 for connecting to the sensor platform 1210, while the add-on system 1001 is within the sensor device 1000. The sensor device connection port 1024 is able to share data and/or power between the circuit board 1110 and the sensor platform 1210.

The add-on system 1001 may also include an external connection port 1026 that provides a readout of the memory of the sensor platform 1210 when the add-on system 1001 is in place.

Referring now to FIG. 11, there is shown a flow diagram of an example method for activating the sensor device 100 according to some embodiments.

At 902, the sensor device 100 may be held proximate to a magnet in order to activate the hall effect sensor on the sensor platform 210.

In some embodiments, the sensor device must be held proximate a magnet for at least 3 seconds to avoid situations where the hall effect sensor is accidentally activated. The sensor platform including the microcontroller takes over the load switch signal from the hall sensor (otherwise if magnet is removed the load switch will turn the battery off again).

At 904, the magnetic field generated by the magnet activates the hall effect sensor located on the sensor platform 210. At 906, the activated hall effect sensor in-turn activates a load switch. The load-switch turns-on the batteries 204a, 204b of the sensor device 100 which supply power to the various electronics located on, or otherwise connected to, the sensor platform 210. At 908, an LED located, for example, on the sensor platform 210, may turn ON to indicate that the sensor device 100 is powered. At 910, the sensor device 100 can be inserted into a fluid conduit to collect fluid and fluid conduit data using one or more sensors located therein. At 912, the sensor device can be removed from the fluid conduit so that sensor data/measurements are retrieved. In particular, the sensor device 100 can be disassembled and an SD card, or micro SD card can be retrieved.

In at least some embodiments, once the sensor device 100 is activated using the magnet, it cannot be otherwise deactivated (i.e. it must be used continuously).

While the above description provides examples of one or more apparatus, methods, or systems, it will be appreciated that other apparatus, methods, or systems may be within the scope of the claims as interpreted by one of skill in the art.

The invention claimed is:

1. A sensor device for measuring fluid and fluid conduit properties, the sensor device comprising:
   an outer capsule for providing fluid-tight containment to an inner compartment in a closed position, wherein the outer capsule comprises a first capsule portion and a second capsule portion;
   an aperture located in the second capsule portion and fluidly connecting the inner compartment to an exterior of the outer capsule;
   a mounting bracket disposed within the inner compartment, the mounting bracket connecting the first capsule portion to the second capsule portion and providing structural integrity and pressure resistivity for the outer capsule;
   at least one pressure sensor constrained between the mounting bracket and an inner surface of the second capsule portion and aligned with the aperture of the second capsule portion, wherein the at least one pressure sensor senses pressure applied by the fluid to the sensor device;
   a power source mounted to the mounting bracket and configured to supply power to the sensor device; and
   a hall effect sensor for activating the sensor device.

2. The sensor device of claim 1, further comprising: a load switch coupled to the power source and the hall effect sensor, wherein the load switch is configured to activate the power source when the hall effect sensor is activated.

3. The sensor device of claim 1, wherein the sensor device is configured to withstand pressures of up to 100 bar.

4. The sensor device of claim 1, wherein the outer capsule is formed of fiber-reinforced polymer plastic.

5. The sensor device of claim 4, wherein the outer capsule is formed of fiber-reinforced nylon plastic.

6. The sensor device of claim 1, wherein the outer capsule is formed of material capable of withstanding temperatures of at least 80° C.

7. The sensor device of claim 1, wherein the at least one pressure sensor further comprises a temperature sensor.

8. The sensor device of claim 1, wherein the power source comprises batteries.

9. The sensor device of claim 1, wherein the at least one pressure sensor and the hall effect sensor are coupled to a sensor platform.

10. The sensor device of claim 1, wherein the power source is connected to a sensor platform using one or more conductive strips, the conductive strips being soldered to the sensor platform.

11. The sensor device of claim 1, wherein the sensor device includes at least one indicator light mounted within the inner compartment, the at least one indicator light indicating the power status of the sensor device.

12. The sensor device of claim 1, wherein at least one of the first capsule portion and the second capsule portion is formed of substantially transparent material.

13. The sensor device of claim 1, wherein the sensor device further comprises a memory for storing data collected by at least one sensor located in the inner compartment.

14. The sensor device of claim 1 further comprising an add-on system for transmitting an electro-magnetic signal that is detected by an external receiver to verify if the sensor device is at a predetermined location.

15. A method of activating a sensor device for measuring fluid and fluid conduit properties, the method comprising:
   placing the sensor device in proximity of a magnetic field, the sensor device comprising:
      an outer capsule for providing fluid-tight containment to an inner compartment in a closed position, wherein the outer capsule comprises a first capsule portion and a second capsule portion;
      a mounting bracket disposed within the inner compartment, the mounting bracket connecting the first capsule portion to the second capsule portion and providing structural integrity and pressure resistivity for the outer capsule;
      at least one pressure sensor constrained between the mounting bracket and an inner surface of the second capsule portion and aligned with an aperture of the second capsule portion; and
      a power source mounted to the mounting bracket;
   activating a hall effect sensor located within the inner compartment of the sensor device;
   triggering a load switch coupled to both the hall effect sensor and the power source, wherein the load switch switches on the power source;
   activating a light indicator to indicate that the sensor device is powered on.

16. The method of claim 15, wherein the magnetic field is generated by a permanent magnet.

17. The method of claim 15, wherein the sensor device is placed in proximity of the magnetic field for at least three seconds.

18. The method of claim 15, further comprising: inserting the sensor device in a fluid conduit and measuring fluid and fluid conduit data using the sensor device.

19. The method of claim 18, further comprising: removing the sensor device from the fluid conduit and retrieving fluid and fluid conduit data from a memory located in the inner compartment.

* * * * *